United States Patent [19]

Murdock et al.

[11] 4,456,552
[45] Jun. 26, 1984

[54] 1,4-BIS(SUBSTITUTED-AMINO)-5,8-DIHYDROXYANTHRAQUINONES AND LEUCO BASES THEREOF

[75] Inventors: Keith C. Murdock, Pearl River, N.Y.; Frederick E. Durr, Ridgewood, N.J.

[73] Assignee: American Cyanamid Company, Stamford, Conn.

[21] Appl. No.: 239,939

[22] Filed: Mar. 2, 1981

Related U.S. Application Data

[60] Division of Ser. No. 63,285, Aug. 2, 1979, Pat. No. 4,278,689, which is a division of Ser. No. 923,602, Jul. 11, 1978, Pat. No. 4,197,249, which is a continuation-in-part of Ser. No. 873,040, Jan. 30, 1978, abandoned, which is a continuation-in-part of Ser. No. 824,872, Aug. 15, 1977, abandoned.

[51] Int. Cl.³ ................ C07C 97/26; A61K 31/125
[52] U.S. Cl. .................................. 260/377; 260/379; 260/380; 424/330
[58] Field of Search ................ 260/377, 379, 380

[56] References Cited

U.S. PATENT DOCUMENTS

| | | | |
|---|---|---|---|
| 3,646,072 | 2/1972 | James | 260/380 |
| 3,857,864 | 12/1974 | Schwander et al. | 260/377 X |
| 3,904,660 | 9/1975 | Doso | 260/380 |
| 4,166,822 | 9/1979 | Hohmann et al. | 260/380 |
| 4,170,564 | 10/1979 | Brendle | 260/379 X |
| 4,197,249 | 4/1980 | Murdock et al. | 260/378 X |
| 4,278,689 | 7/1981 | Murdock et al. | 424/330 |
| 4,296,030 | 10/1981 | Lang, Jr. et al. | 260/380 X |
| 4,310,666 | 1/1982 | Zee-Cheng et al. | 260/378 X |

FOREIGN PATENT DOCUMENTS

| | | | |
|---|---|---|---|
| 1157506 | 7/1964 | United Kingdom . | |
| 1475081 | 6/1977 | United Kingdom | 260/380 |

Primary Examiner—Thomas A. Waltz
Attorney, Agent, or Firm—Edward A. Conroy, Jr.

[57] ABSTRACT

This disclosure describes symmetrical 1,4-bis(substituted-amino)-5,8-dihydroxyanthraquinones useful as chelating agents and for inhibiting the growth of transplanted mouse tumors.

5 Claims, No Drawings

1,4-BIS(SUBSTITUTED-AMINO)-5,8-DIHYDROX-YANTHRAQUINONES AND LEUCO BASES THEREOF

CROSS REFERENCE TO RELATED APPLICATIONS

This application is a division of our application Ser. No. 63,285, filed Aug. 2, 1979, now U.S. Pat. No. 4,278,689, which is a division of our application Ser. No. 923,602, filed July 11, 1978, now U.S. Pat. No. 4,197,249, which is a continuation-in-part of our application Ser. No 873,040, filed Jan. 30, 1978, now abandoned, which is a continuation-in-part of our application Ser. No. 824,872, filed Aug. 15, 1977, now abandoned.

BRIEF SUMMARY OF THE INVENTION

This invention relates to new organic compounds and, more particularly, is concerned with novel symmetrical 1,4-bis(substituted-amino)-5,8-dihydroxyanthraquinones which may be represented by the following general formula:

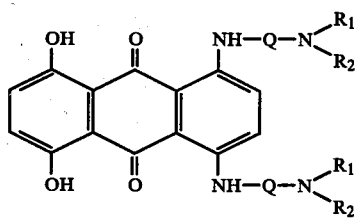

wherein Q is a divalent moiety selected from the group consisting of those of the formulae:

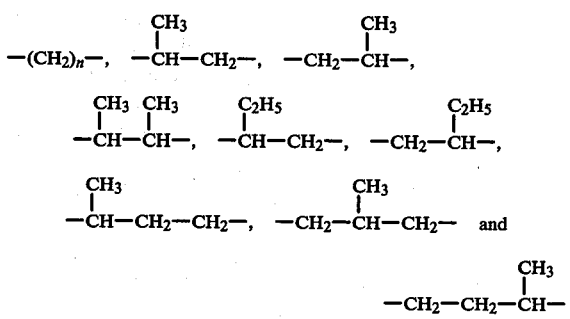

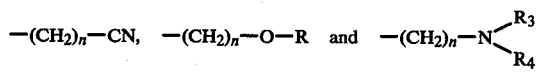

wherein n is an integer from 2 to 4, inclusive; $R_1$ and $R_2$ are each individually selected from the group consisting of hydrogen, alkyl having from 1 to 4 carbon atoms, monohydroxyalkyl having from 2 to 4 carbon atoms and wherein the carbon atom alpha to the nitrogen atom may not bear an hydroxy group, dihydroxyalkyl having from 3 to 6 carbon atoms and wherein the carbon atom alpha to the nitrogen atom may not bear an hydroxy group, formyl, alkanoyl having from 2 to 4 carbon atoms, trifluoroacetyl and moieties of the formulae:

$$-(CH_2)_n-CN, \quad -(CH_2)_n-O-R \quad \text{and} \quad -(CH_2)_n-N\begin{matrix}R_3\\R_4\end{matrix}$$

wherein n is an integer from 2 to 4, inclusive, R is alkyl having from 1 to 4 carbon atoms, and $R_3$ and $R_4$ are each individually selected from the group consisting of hydrogen, alkyl having from 1 to 4 carbon atoms, and monohydroxyalkyl having from 2 to 4 carbon atoms and wherein the carbon atom alpha to the nitrogen atom may not bear an hydroxy group, and $R_3$ and $R_4$ taken together with their associated N(itrogen) is morpholino, chiomorpholino, piperazino, 4-methyl-1-piperazino or a moiety of the formula:

wherein m is an integer from 2 to 6, inclusive; with the first proviso that the ratio of the total number of carbon atoms to the sum of the total number of oxygen atoms plus the total number of nitrogen atoms in the side chains at the 1-position and the 4-position may not exceed 4 and with the second proviso that $R_1$ and $R_2$ may not both be hydrogen or alkyl. Suitable monohydroxyalkyl and dihydroxyalkyl groups contemplated by the present invention are, for example, β-hydroxyethyl, β-hydroxypropyl, γ-hydroxypropyl, 2,3-dihydroxypropyl, 2,4-dihydroxybutyl, and the like. Also included within the purview of the present invention are the leuco bases and tautomers thereof which may be represented by the following general formulae:

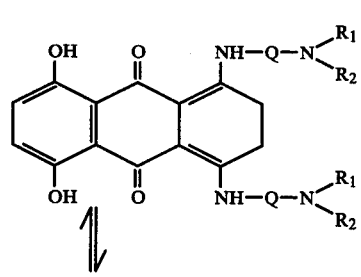

(II, leuco bases)

⇅

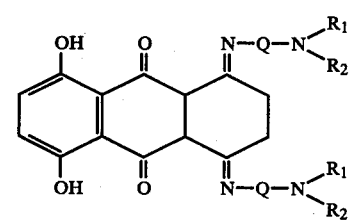

(III, tautomeric form)

wherein $R_1$, $R_2$ and Q are as hereinabove defined.

DETAILED DESCRIPTION OF THE INVENTION

The novel compounds of the present invention are obtainable as reddish brown to blue black crystalline materials having characteristic melting points and absorption spectra and which may be purified by leaching with lower alkanols since many of the free bases are insoluble in water and some of them are insoluble in most organic solvents. The organic bases of this invention (I, II and III) form non-toxic acid-addition salts with a variety of pharmacologically acceptable organic and inorganic salt-forming reagents. Thus, acid-addition salts, formed by admixture of the organic free base with 1,2 or up to eight equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention may be readily prepared in accordance with the following reaction scheme:

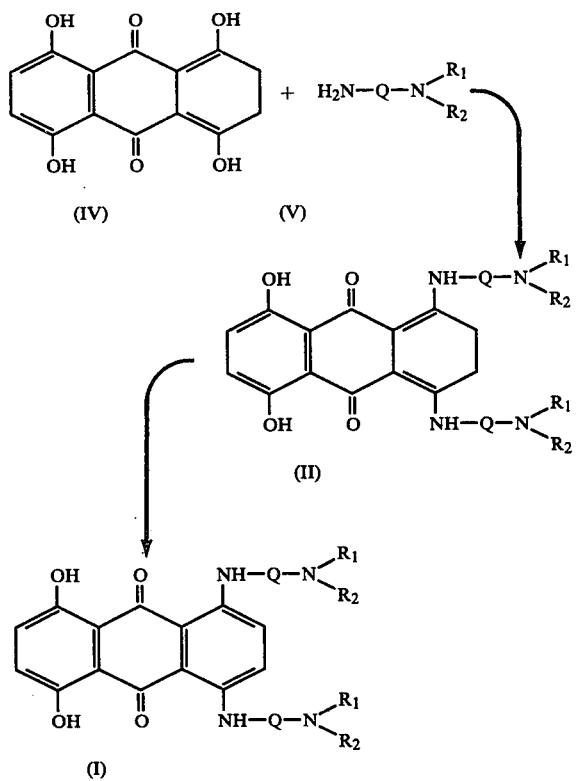

wherein $R_1$, $R_2$ and Q are as hereinabove defined. In accordance with this reaction scheme, leuco 1,4,5,8-tetrahydroxyanthraquinone (IV) is condensed with an appropriate alkylene diamine (V) in a solvent such as N,N,N',N''-tetramethylethylenediamine, methanol, ethanol, water, dimethylformamide, or mixtures thereof at from about 40° C. to about 60° C. under an atmosphere of nitrogen for several hours to produce the corresponding leuco bases (II). The leuco bases (II) may be readily oxidized to the fully aromatic derivatives (I) by a variety of methods such as air oxidation or treatment with hot nitrobenzene, or treatment with chloranil, hydrogen peroxide, or sodium perborate.

The novel compounds described herein are useful as chelating, complexing or sequestering agents. The complexes formed with polyvalent metal ions are particularly stable and usually soluble in various organic solvents. These properties, of course, render them useful for a variety of purposes wherein metal ion contamination presents a problem; e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by these materials and as metal carriers. Other uses common to sequestering agents are also apparent for these compounds. In addition, the leuco bases (II) are useful as intermediates in the preparation of the fully aromatic derivatives (I).

The novel compounds of the present invention also possess the property of inhibiting the growth of transplanted mouse tumors as established by the following tests.

LYMPHOCYTIC LEUKEMIA P388 TEST

The animals used are DBA/2 mice all of one sex, weighing a minimum of 17 g. and all within a 3 gram weight range. There are 5 or 6 animals per test group. The tumor transplant is by intraperitoneal injection of 0.1 ml. of dilute ascitic fluid containing $10^6$ cells of lymphocytic leukemia P388. The test compounds are administered intraperitoneally on days one, 5 and 9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil given as a 60-mg./kg. injection. The results of this test with representative compounds of the present invention appear in Table I. The criterion for efficacy is $T/C \times 100 \geq 125\%$.

TABLE I

| Compound | Lymphocytic Leukemia P388 Test | | |
|---|---|---|---|
| | Dose mg./kg. | Median Survival Time (Days) | T/C × 100 (Percent) |
| Leuco-1,4-bis[(2-dimethylamino- | 100 | 14.5 | 145 |
| ethyl)amino]-5,8-dihydroxy- | 50 | 14.5 | 145 |
| anthraquinone | 25 | 9.0 | 90 |
| | 12 | 7.5 | 75 |
| | 6 | 6.0 | 60 |
| | 3 | 4.5 | 45 |
| | 1.5 | 3.0 | 30 |
| Control | 0 | 0.0 | — |
| 5-Fluorouracil | 60 | 9.0 | 90 |
| 1,4-Bis[(2-dimethylaminoethyl)- | 50 | 15.0 | 178 |
| amino]-5,8-dihydroxy-anthraquinone | 25 | 10.5 | 128 |
| | 12 | 13.0 | 156 |
| | 6 | 11.0 | 133 |
| | 3 | 9.5 | 117 |
| Control | 0 | 4.0 | — |
| 5-Fluorouracil | 60 | 9.5 | 117 |
| Leuco-1,4-bis(2-morpholinoethyl- | 200 | 3.0 | 37 |
| amino)-5,8-dihydroxy-anthraquinone | 100 | 2.0 | 26 |

TABLE I-continued

Lympyhocytic Leukemia P388 Test

| Compound | Dose mg./kg. | Median Survival Time (Days) | T/C × 100 (Percent) |
|---|---|---|---|
| | 50 | 11.0 | 116 |
| | 25 | 12.0 | 126 |
| Control | 0 | 9.5 | — |
| 5-Fluorouracil | 60 | 19.5 | 205 |
| 1,4-Bis(2-morpholinoethylamino)- | 200 | 14.0 | 147 |
| 5,8-dihydroxy-anthraquinone | 100 | 12.0 | 126 |
| Control | 0 | 9.5 | — |
| 5-Fluorouracil | 60 | 19.5 | 205 |
| Leuco-1,4-bis[(2-diethylamino- | 200 | 17.0 | 179 |
| ethyl)amino]-5,8-dihydroxy-anthra- | 100 | 17.0 | 179 |
| quinone | 50 | 15.0 | 158 |
| | 25 | 13.0 | 137 |
| | 12 | 12.0 | 126 |
| Control | 0 | 9.5 | — |
| 5-Fluorouracil | 60 | 19.5 | 205 |
| 1,4-Bis[(2-diethylaminoethyl)- | 200 | 20.0 | 210 |
| amino]-5,8-dihydroxy-anthraquinone | 100 | 18.0 | 189 |
| | 50 | 15.0 | 158 |
| | 25 | 16.0 | 168 |
| | 12 | 12.0 | 126 |
| Control | 0 | 9.5 | — |
| 5-Fluorouracil | 60 | 19.5 | 205 |
| Leuco-1,4-bis[[2-(1-pyrrolidinyl)- | 200 | 23.0 | 209 |
| ethyl]amino]-5,8-dihydroxy-anthra- | 100 | 19.0 | 173 |
| quinone | 50 | 16.0 | 145 |
| | 25 | 15.0 | 136 |
| Control | 0 | 11.0 | — |
| 5-Fluorouracil | 60 | 20.0 | 182 |
| 1,4-Bis[[2-(1-pyrrolidinyl)ethyl]- | 100 | 24.0 | 218 |
| amino]-5,8-dihydroxy-anthraquinone | 50 | 23.0 | 209 |
| | 25 | 21.0 | 191 |
| | 12 | 18.0 | 164 |
| Control | 0 | 11.0 | — |
| 5-Fluorouracil | 60 | 20.0 | 182 |
| 1,4-Bis[(3-dimethylaminopropyl)- | 50 | 15.5 | 129 |
| amino]-5,8-dihdyroxy-anthraquinone | 25 | 15.5 | 129 |
| | 12 | 15.0 | 125 |
| Control | 0 | 12.0 | — |
| 5-Fluorouracil | 60 | 19.5 | 162 |
| Leuco-1,4-bis[(2-aminoethyl)- | 100 | 19.0 | 158 |
| amino]-5,8-dihydroxy-anthraquinone | 50 | 23.0 | 192 |
| | 25 | 19.0 | 158 |
| | 12 | 18.0 | 150 |
| Control | 0 | 12.0 | — |
| 6-Fluorouracil | 60 | 19.5 | 162 |
| Leuco-1,4-bis(3-aminopropylamino)- | 200 | 18.0 | 150 |
| 5,8-dihydroxy-anthraquinone | 100 | 18.0 | 150 |
| | 50 | 16.0 | 133 |
| | 25 | 18.0 | 150 |
| | 12 | 16.0 | 133 |
| Control | 0 | 12.0 | — |
| 6-Fluorouracil | 60 | 19.5 | 162 |
| Leuco-1,4-bis[2-(2-methylamino- | 200 | 2.0 | 18.0 |
| ethylamino)ethylamino]-5,8-dihy- | 100 | 25.0 | 236.0 |
| droxyanthraquinone | 50 | 28.0 | 255.0 |
| | 1 | 21.0 | 191.0 |
| | 12.0 | 16.0 | 145.0 |
| | 6.2 | 15.0 | 136 |
| Control | 0 | 11.0 | — |
| 5-Fluorouracil | 60 | 17.0 | 170 |
| Leuco-1,4-bis[2-dimethylaminopro- | 200 | 18.0 | 200 |
| pylamino]-5,8-dihydroxyanthraqui- | 100 | 15.0 | 167 |
| none | 50 | 14.0 | 150 |
| | 25 | 13.0 | 144 |
| | 12.5 | 11.0 | 122 |
| Control | 0 | 9.0 | — |
| 5-Fluorouracil | 60 | 18.5 | 206 |
| 1,4-Bis[2-(2-hydroxyethylamino) | 12.5 | 13.0 | 130 |
| ethylamino]-5,8-dihydroxyanthra- | 6.2 | 20.0 | 200 |
| quinone Dihydrochloride | 3.1 | 22.0 | 220 |
| | 1.5 | >29.0 | >290 |
| | 0.78 | >29.0 | >290 |
| | 0.39 | 27.0 | 270 |
| | 0.19 | 25.0 | 250 |
| | 0.09 | 21.0 | 210 |
| | 0.04 | 20.0 | 200 |
| Control | 0 | 10.0 | — |
| 5-Fluorouracil | 60 | 20.0 | 200 |
| Leuco-1,4-bis[2-(1-piperazinyl) | 200 | 7.0 | 78 |

TABLE I-continued

Lympyhocytic Leukemia P388 Test

| Compound | Dose mg./kg. | Median Survival Time (Days) | T/C × 100 (Percent) |
|---|---|---|---|
| ethylamino]-5,8-dihydroxyanthra- | 100 | 21.0 | 233 |
| quinone | 50 | 16.0 | 178 |
| | 25 | 15.0 | 167 |
| | 12.5 | 14.0 | 156 |
| Control | 0 | 9.0 | — |
| 5-Fluorouracil | 60 | 18.5 | 206 |
| 1,4-Bis[2-(methylamino)ethylamino]- | 25 | 9.0 | 86 |
| 5,8-dihydroxyanthraquinone dihydro- | 12.5 | 16.0 | 152 |
| chloride | 6.2 | 20.0 | 190 |
| | 3.1 | 22.0 | 210 |
| | 1.5 | 22.5 | 214 |
| | 0.78 | 18.5 | 176 |
| | 0.39 | 19.5 | 186 |
| | 0.19 | 18.5 | 176 |
| | 0.09 | 18.0 | 171 |
| | 0.04 | 17.0 | 162 |
| Control | 0 | 10.5 | — |
| 5-Fluorouracil | 60 | 18.0 | 171 |
| Leuco-1,4-bis[2-(2-hydroxyethylamino) | 25 | 12.0 | 114 |
| ethylamino]-5,8-dihydroxyanthraquinone | 12.5 | 23.5 | 224 |
| | 6.2 | 23.0 | 219 |
| | 3.1 | 26.0 | 248 |
| | 1.5 | >30.0 | >286 |
| | 0.78 | 28.0 | 267 |
| | 0.39 | 22.0 | 209 |
| | 0.19 | 21.5 | 205 |
| | 0.09 | 21.5 | 205 |
| | 0.04 | 18.5 | 176 |
| Control | 0 | 10.5 | — |
| 6-Fluorouracil | 60 | 18.0 | 171 |
| Leuco-1,4-bis(4-aminobutyl- | 400 | 20.0 | 190 |
| amino)-5,8-dihydroxyanthra- | 300 | 18.0 | 171 |
| quinone | 200 | 17.0 | 162 |
| | 100 | 14.0 | 133 |
| Control | 0 | 10.5 | — |
| 5-Fluorouracil | 60 | 17.5 | 162 |
| Leuco-1,4-bis[2-(methyl- | 50 | 6.0 | 55 |
| amino)ethylamino]-5,8- | 25 | 19.0 | 173 |
| dihydroxyanthraquinone | 12.5 | 19.0 | 173 |
| | 6.2 | 21.0 | 191 |
| | 3.1 | 15.0 | 136 |
| | 1.5 | 13.0 | 118 |
| Control | 0 | 11.0 | — |
| 5-Fluorouracil | 60 | 18.5 | 168 |
| Leuco-1,4-bis[2-(2-isopropyl- | 100 | 8.0 | 73 |
| amino)ethylamino]-5,8-dihy- | 50 | 19.0 | 173 |
| droxyanthraquinone | 25 | 17.0 | 155 |
| | 12.5 | 15.0 | 136 |
| Control | 0 | 11.0 | — |
| 5-Fluorouracil | 60 | 20.5 | 186 |
| 1,4-Bis[2-(2-aminoethylamino) | 200 | 17.0 | 162 |
| ethylamino]-5,8-dihydroxyanth- | 100 | 16.0 | 152 |
| raquinone | 50 | 14.0 | 133 |
| | 25 | 13.0 | 124 |
| Control | 0 | 10.5 | — |
| 5-Fluorouracil | 60 | 17.0 | 162 |
| Leuco-1,4-[2-[di(β-hydroxy- | 200 | 19.0 | 190 |
| ethyl)amino]ethylamino-5,8- | 100 | 17.0 | 170 |
| dihydroxyanthraquinone | 50 | 16.0 | 160 |
| | 25 | 15.0 | 150 |
| | 12.5 | 13.5 | 135 |
| | 6.2 | 12.0 | 120 |
| Control | 0 | 10.0 | — |
| 5-Fluorouracil | 40 | 18.0 | 180 |
| 1,4-Bis[2-(2-hydroxy-1-pro- | 25 | 12.0 | 120 |
| pylamino)ethylamino]1,4-di- | 12.5 | 24.0 | 240 |
| hydroxyanthraquinone dihy- | 6.2 | 23.0 | 230 |
| drochloride | 3.1 | 22.0 | 220 |
| | 1.56 | 19.0 | 190 |
| | 0.78 | 19.0 | 190 |
| | 0.39 | 17.5 | 175 |
| Control | 0 | 10.0 | — |
| 5-Fluorouracil | 40 | 18.0 | 180 |
| 1,4-Bis[2, [2-(1-morpholino)ethyl- | 200 | 9.5 | 95 |
| amino]ethylamino]5,8-dihydroxyan- | 100 | 20.0 | 200 |
| thraquinone tetrahydrochloride | 50 | 18.5 | 185 |
| | 25 | 19.5 | 195 |
| | 12.5 | 15.0 | 150 |
| | 6.2 | 14.0 | 140 |

TABLE I-continued

Lympyhocytic Leukemia P388 Test

| Compound | Dose mg./kg. | Median Survival Time (Days) | T/C × 100 (Percent) |
|---|---|---|---|
| | 3.1 | 13.0 | 130 |
| Control | 0 | 10.0 | — |
| 5-Fluorouracil | 40 | 18.0 | 180 |
| 1,4-Bis[2-(3-hydroxy-1-propyl-amino)ethylamino]5,8-dihydroxy-anthraquinone dihydrochloride | 25 | 8.5 | 77 |
| | 12.5 | >10.0 | >273 |
| | 6.25 | 26.0 | 236 |
| | 3.1 | 25.0 | 227 |
| | 1.56 | 22.0 | 200 |
| | 0.78 | 21.5 | 195 |
| Control | 0 | 11.0 | — |
| 5-Fluorouracil | 40 | 18.0 | 164 |
| Leuco = 1,4 = bis[p = (3 = hydroxy = 1 = propylamino)ethylamino]5,8-dihydroxyanthraquinone | 200 | 14.0 | 127 |
| | 100 | 38.0 | 345 |
| | 50 | 34.0 | 309 |
| | 25 | 22.0 | 200 |
| | 12.5 | 19.5 | 177 |
| | 6.25 | 16.5 | 150 |
| | 3.1 | 18.5 | 168 |
| | 1.56 | 19.5 | 177 |
| | 0.78 | 18.0 | 164 |
| Control | 0 | 11.0 | — |
| 5-Fluorouracil | 40 | 17.0 | 155 |
| 1,4-Bis[2-[di($\beta$-hydroxyethyl)-amino]ethylamino]5,8-dihydrox-yanthraquinone dihydrochloride | 200 | >30.0 | >333 |
| | 100 | 22.0 | 244 |
| | 50 | 20.5 | 228 |
| | 25 | 21.5 | 239 |
| | 12.5 | 18.5 | 206 |
| | 6.2 | 18.5 | 206 |
| | 3.1 | 19.0 | 211 |
| | 1.56 | 16.0 | 178 |
| | 0.78 | 14.5 | 161 |
| Control | 0 | 9.0 | — |
| 5-Fluorouracil | 60 | 20.5 | 228 |
| Leuco-1,4-bis[3-(2-hydroxy-ethylamino)-1-propylamino]-5,8-dihydroxyanthraquinone | 200 | 33.5 | 305 |
| | 100 | 27.5 | 250 |
| | 50 | 25.0 | 227 |
| | 25 | 18.5 | 168 |
| | 12.5 | 19.0 | 173 |
| | 6.25 | 18.0 | 164 |
| | 3.12 | 15.0 | 136 |
| Control | 0 | 11.0 | — |
| 5-Fluorouracil | 40 | 17.5 | 159 |
| Leuco-1,4-bis[2-(2-hydroxy-1-propylamino)ethylamino]-1,4-dihydroxyanthraquinone | 200 | 9.0 | 82 |
| | 100 | 26.5 | 241 |
| | 50 | 24.0 | 218 |
| | 25 | 20.5 | 186 |
| | 12.5 | 21.5 | 195 |
| | 6.25 | 20.0 | 182 |
| Control | 0 | 11.0 | — |
| 5-Fluorouracil | 40 | 17.5 | 159 |
| 1,4-Bis[3-(2-hydroxyethyl-amino)-1-propylamino]5,8-dihydroxyanthraquinone dihydrochloride | 100 | 12.5 | 114 |
| | 50 | 32.0 | 291 |
| | 25 | 26.5 | 241 |
| | 12.5 | 22.5 | 205 |
| | 6.25 | 19.0 | 173 |
| | 3.12 | 19.0 | 173 |
| | 1.56 | 16.0 | 145 |
| | 0.78 | 15.0 | 136 |
| Control | 0 | 11.0 | — |
| 5-Fluorouracil | 40 | 17.5 | 159 |
| 1,4-Bis[2-(1-aziridino)ethyl-amino]-5,8-dihydroxyanthra-quinone | 100 | 28.5 | 285 |
| | 50 | 21.5 | 215 |
| | 25 | 20.0 | 200 |
| | 12.5 | 20.5 | 205 |
| | 6.25 | 18.5 | 185 |
| | 3.12 | 19.5 | 195 |
| | 1.56 | 17.0 | 170 |
| | 0.78 | 14.0 | 140 |
| Control | 0 | | — |
| 5-Fluorouracil | 60 | 20.5 | 205 |
| 1,4-Bis[2-(2-methylaminoethyl-amino)ethylamino]5,8-dihydrox-yanthraquinone tetrahydrochloride | 100 | 22.0 | 220 |
| | 50 | 22.0 | 220 |
| | 25 | 19.5 | 195 |
| | 12.5 | 17.0 | 170 |
| | 6.25 | 16.0 | 160 |
| | 1.12 | 13.5 | 135 |
| | 1.56 | 13.0 | 130 |
| Control | 0 | 10.0 | — |

TABLE I-continued

| | Lympyhocytic Leukemia P388 Test | | |
|---|---|---|---|
| Compound | Dose mg./kg. | Median Survival Time (Days) | T/C × 100 (Percent) |
| 5-Fluorouracil | 40 | 16.0 | 160 |
| 1,4-Bis(2-aminoethylamino)- | 12.5 | 8.0 | 73 |
| 5,8-dihydroxyanthraquinone | 6.2 | 15.5 | 141 |
| dihydrochloride | 3.1 | 30.0 | 273 |
| | 1.56 | 20.0 | 182 |
| | 0.78 | 24.5 | 223 |
| | 0.39 | 25.5 | 232 |
| | 0.19 | 23.0 | 209 |
| Control | 0 | 11.0 | — |
| 5-Fluorouracil | 60 | 20.5 | 186 |

LYMPHOCYTIC LEUKEMIA P388 TEST

The procedure used is the same as for the previously described test for lymphocytic leukemia P388 except that the test compounds are administered orally at various doses rather than intraperitoneally. The results of this test with typical compounds of the present invention appear in Table II. The criterion for efficacy is T/C×100≧125%.

tumor is homogenized in 10 ml. of cold balanced salt solution and a 0.5-ml. aliquot of the homogenate is implanted intraperitoneally into each of the test mice. The test compounds are administered intraperitoneally on days one through 9 (relative to tumor inoculation) at various doses. The animals are weighed and survivors are recorded on a regular basis for 60 days. The median survival time and the ratio of survival time for treated (T)/control (C) animals are calculated. The positive

TABLE II

| | Lymphocytic Leukemia P388 Test (Oral Drug Administration) | | |
|---|---|---|---|
| Compound | Dose mg./kg. | Median Survival Time (Days) | T/C × 100 (Percent) |
| Leuco-1,4-bis[(2-dimethylamino- | 50 | 16.0 | 160 |
| ethyl)amino]-5,8-dihydroxy-anthra- | 25 | 13.5 | 135 |
| quinone | 12 | 12.5 | 125 |
| Control | 0 | 10.0 | — |
| 5-Fluorouracil* | 60 | 19.0 | 190 |
| 1,4-Bis[(2-dimethylaminoethyl)- | 12 | 16.0 | 139 |
| amino]-5,8-dihydroxy-anthraquinone | 6 | 16.0 | 139 |
| | 3 | 15.0 | 130 |
| Control | 0 | 11.5 | — |
| 5-Fluorouracil* | 60 | 20.0 | 174 |

*5-Fluorouracil administered intraperitoneally.

MELANOTIC MELANOMA B16

The animals used are C57BC/6 mice, all of the same sex, weighing a minimum of 17 g. and all within a 3-g. weight range. There are normally 10 animals per test group. A one-gram portion of melanotic melanoma B16 control compound is 5-fluorouracil given as a 20-mg./kg. injection. The results of this test with representative compounds of the present invention appear in Table III. The criterion for efficacy is T/C×100≧125%.

TABLE III

| | Melanotic Melanoma B16 Test | | |
|---|---|---|---|
| Compound | Dose mg./kg. | Median Survival Time (Days) | T/C × 100 (Percent) |
| Leuco-1,4-bis[(2-dimethylamino- | 25 | 15.0 | 51 |
| ethyl)amino]-5,8-dihydroxy-anthra- | 12 | 13.0 | 39 |
| quinone | 6 | 11.5 | 30 |
| | 3 | 11.0 | 27 |
| Control | 0 | 6.5 | — |
| 5-Fluorouracil | 20 | 15.0 | 51 |
| 1,4-Bis[(2-dimethylaminoethyl)- | 25 | 14.5 | 36 |
| amino]-5,8-dihydroxy-anthraquinone | 12 | 18.5 | 58 |
| | 6 | 17.0 | 50 |
| | 3 | 15.5 | 42 |
| Control | 0 | 8.0 | — |
| 5-Fluorouracil | 20 | 16.0 | 44 |
| Leuco-1,4-bis[(2-diethylamino- | 50 | 13.0 | 39 |
| ethyl)amino]-5,8-dihydroxy-anthra- | | | |
| quinone | | | |
| Control | 0 | 6.5 | — |
| 5-Fluorouracil | 20 | 15.0 | 51 |
| 1,4-Bis[(2-diethylaminoethyl)- | 50 | 10.5 | 25 |
| amino]-5,8-dihydroxy-anthraquinone | | | |
| Control | 0 | 6.5 | — |
| 5-Fluorouracil | 20 | 15.0 | 51 |
| Leuco-1,4-bis[[2-(1-pyrrolidinyl)- | 50 | 13.0 | 44 |
| ethyl]amino]-5,8-dihydroxy-anthra- | 25 | 12.0 | 37 |
| quinone | 12 | 11.0 | 31 |

TABLE III-continued

Melanotic Melanoma B16 Test

| Compound | Dose mg./kg. | Median Survival Time (Days) | T/C × 100 (Percent) |
|---|---|---|---|
| Control | 0 | 16.0 | — |
| 5-Fluorouracil | 20 | 26.5 | 166 |
| 1,4-Bis[[2-(1-pyrrolidinyl)ethyl]-amino]-5,8-dihydroxy-anthraquinone | 25 | 24.5 | 153 |
|  | 12 | 22.0 | 137 |
|  | 6 | 22.0 | 137 |
| Control | 0 | 16.0 | — |
| 5-Fluorouracil | 20 | 26.5 | 166 |
| 1,4-Bis[(3-dimethylaminopropyl)-amino]-5,8-dihydroxy-anthraquinone | 25 | 20.0 | 125 |
| Control | 0 | 16.0 | — |
| 5-Fluorouracil | 20 | 26.5 | 166 |
| Leuco-1,4-bis[(2-aminoethyl)-amino]-5,8-dihydroxy-anthraquinone | 12 | 32.0 | 200 |
| Control | 0 | 16.0 | — |
| 5-Fluorouracil | 20 | 26.5 | 166 |
| Leuco-1,4-bis(3-aminopropylamino)-5,8-dihydroxy-anthraquinone | 50 | 31.5 | 197 |
|  | 25 | 27.0 | 169 |
|  | 12 | 23.5 | 147 |
|  | 6 | 22.5 | 141 |
| Control | 0 | 16.0 | — |
| 5-Fluorouracil | 20 | 26.5 | 166 |
| Leuco-1,4-bis[2-(2-methylamino-ethylamino]-5,8-dihydroxyanthra-quinone | 50 | 12.5 | 73 |
|  | 25 | 35.0 | 206 |
|  | 12.5 | 39.5 | 232 |
|  | 6.2 | 28.5 | 168 |
| Control | 0 | 17.0 | — |
| 5-Fluorouracil | 20 | 30.0 | 176 |
| Leuco-1,4-bis[2-(1-piperazinyl)ethylamino]-5,8-dihydroxyanthra-quinone | 50 | 34.5 | 203 |
|  | 25 | 30.5 | 179 |
|  | 12.5 | 26.0 | 153 |
|  | 6 | 22.0 | 129 |
|  | 3 | 20.5 | 121 |
| Control | 0 | 17.0 | — |
| 5-Fluorouracil | 20.0 | 30 | 176 |
| 1,4-Bis[2-(2-aminoethylamino)ethylamino]-5,8-dihydroxyanthra-quinone | 50 | 24.0 | 150 |
|  | 25 | 22.5 | 141 |
|  | 12 | 22.0 | 138 |
|  | 6 | 20.0 | 125 |
| Control | 0 | 16.0 | — |
| 5-Fluorouracil | 20 | 27.0 | 169 |
| Leuco-1,4-bis[2-dimethylamino-propylamino]-5,8-dihydroxyanthra-quinone | 100 | 21.0 | 124 |
|  | 50 | 28.5 | 168 |
|  | 25 | 24.5 | 144 |
|  | 12.5 | 20.5 | 121 |
|  | 6 | 19.5 | 115 |
| Control | 0 | 17.0 | — |
| 5-Fluorouracil | 20 | 30.0 | 176 |
| 1,4-Bis[2-(2-hydroxyethylamino)ethylamino]-5,8-dihydroxyanthra-quinone dihydrochloride | 12 | 11.0 | 73 |
|  | 6 | 15.0 | 100 |
|  | 3 | >28.5 | >190 |
|  | 1.5 | >34.0 | >227 |
|  | 0.7 | >34.0 | >227 |
|  | 0.3 | 34.0 | 227 |
| Control | 0 | 15.0 | — |
| 5-Fluorouracil | 60 | 23.0 | 153 |
| Leuco-1,4-bis[2-(2-isopropylamino)ethylamino]-5,8-dihydroxyanthra-quinone | 50 | 6.5 | 39 |
|  | 25 | 31.0 | 188 |
|  | 12 | 30.0 | 182 |
|  | 6 | 25.0 | 151 |
| Control | 0 | 16.5 | — |
| 5-Fluorouracil | 20 | 16.5 | 100 |
| 1,4-Bis[2-(methylamino)ethyl-amino]-5,8-dihydroxyanthra-quinone dihydrochloride | 12.5 | 11.5 | 59 |
|  | 6.2 | 26.5 | 136 |
|  | 3.1 | 49.0 | 251 |
|  | 1.5 | 33.0 | 169 |
|  | 0.78 | 35.0 | 179 |
|  | 0.39 | 25.0 | 128 |
|  | 0.19 | 29.5 | 151 |
| Control | 0 | 19.5 | — |
| 5-Fluorouracil | 60 | 25.0 | 128 |
| Leuco-1,4-bis(4-aminobutyl-amino)-5,8-dihydroxyanthra-quinone | 100 | 21.0 | 124 |
|  | 50 | 20.0 | 118 |
|  | 25 | 18.5 | 109 |
|  | 12 | 16.0 | 94 |
| Control | 0 | 17.0 | — |
| 5-Fluorouracil | 20 | 30.0 | 176 |
| Leuco-1,4-bis[2-(2-hydroxy-ethylamino(ethylamino]-5,8-dihydroxyanthraquinone | 6 | 9.5 | 59 |
|  | 3 | 20.5 | 128 |
|  | 1.5 | 30.0 | 187 |

TABLE III-continued

Melanotic Melanoma B16 Test

| Compound | Dose mg./kg. | Median Survival Time (Days) | T/C × 100 (Percent) |
| --- | --- | --- | --- |
|  | 0.75 | 28.5 | 178 |
|  | 0.37 | 22.0 | 137 |
| Control | 0 | 16.0 | — |
| 5-Fluorouracil | 20 | 27.5 | 172 |
| Leuco-1,4-bis[2-(methylamino)ethylamino]-5,8-dihydroxyanthraquinone | 12 | 28.0 | 175 |
|  | 6 | 32.5 | 203 |
|  | 3 | 31.0 | 194 |
|  | 1.5 | 36.0 | 225 |
|  | 0.7 | 27.5 | 172 |
| Control | 0 | 16.0 | — |
| 5-Fluorouracil | 20 | 27.5 | 172 |

RIDGWAY OSTEOGENIC SARCOMA

The animals used are AKD$_2$F$_1$/J mice, all of the same sex, weighing a minimum of 17 g. and all within a three-gram weight range. There are normally 8 animals per test group. The tumor is administered subcutaneously by trocar as five 2-mm. fragments per mouse. The test compounds are administered intraperitoneally every 4 days for a total of 6 inoculations beginning on day 15 (relative to tumor inoculation) at various doses. The animals are weighed and survivors are recorded on a regular basis for 90 days. The regression of tumors is recorded in all test animals. Table IV gives the results of this test with a representative compound of this invention in terms of the percentage of animals showing tumor regression.

carbon atom alpha to the nitrogen atom may not bear an hydroxy group, dihydroxyalkyl having from 3 to 6 carbon atoms and wherein the carbon atom alpha to the nitrogen atom may not bear an hydroxy group or a moiety of the formula:

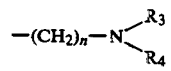

wherein n, R$_3$ and R$_4$ are as hereinbefore defined; with the proviso that the ratio of the total number of carbon atoms to the sum of the total number of oxygen atoms plus the total number of nitrogen atoms in each of the side chains at the 1-position and the 4-position may not exceed four. The preferred embodiment includes the

TABLE IV

Ridgway Osteogenic Sarcoma

| Compound | Dose (mg./kg.) | 1 Day Before Therapy | | 7 Days After Therapy Stopped | | | | 63 Days After Therapy Stopped | |
| --- | --- | --- | --- | --- | --- | --- | --- | --- | --- |
|  |  | No. Mice Per Group | Tumor (mm.) 2 | No. Without Tumors/No. Survivors | Tumor (mm.) 2 | % Inhibition Tumor Growth | % Showing 50% Tumor Regression | Median Survival (Days) | T/C (Percent) |
| Placebo | — | 8 | 64 | 0/5 | 1189 |  | 0 | 44.5 |  |
| 1,4-Bis[(2-dimethylamino-ethyl)amino]-5,8-dihydroxy-anthraquinone | 100 | 7 | 77 | 2/5 | 52 | 96 | 28 | 48 | 108 |
|  | 50 | 8 | 68 | 2/6 | 263 | 78 | 25 | 92.5 | 208 |
|  | 25 | 8 | 82 | 0/8 | 653 | 41 | 0 | 78 | 175 |
|  | 12 | 7 | 84 | 0/3 | 470 | 61 | 0 | 37 | 83 |
|  | 6 | 7 | 83 | 0/6 | 960 | 19 | 0 | 57.5 | 129 |
| Methotrexate | 25 | 8 | 51 | 1/6 | 546 | 54 | 12 | 52.5 | 118 |
|  | 12 | 8 | 52 | 0/5 | 916 | 23 | 0 | 49 | 110 |
|  | 6 | 8 | 54 | 0/4 | 758 | 36 | 0 | 46 | 103 |
| Vincristine | 1.5 | 8 | 42 | 4/4 | 0 | 100 | 100 | 68 | 153 |
|  | 1.0 | 6 | 99 | 6/6 | 0 | 100 | 100 | 85 | 191 |
|  | 0.5 | 7 | 94 | 4/7 | 77 | 93 | 57 | 83 | 186 |

A preferred embodiment of the present invention may be represented by the following general formula:

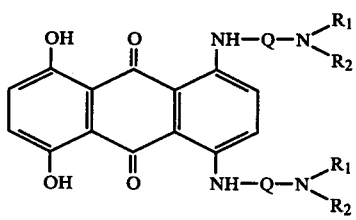

wherein Q is as hereinbefore defined; R$_1$ is hydrogen, alkyl having from 1 to 4 carbon atoms or monohydroxyalkyl having from 2 to 4 carbon atoms wherein the carbon atom alpha to the nitrogen atom may not bear an hydroxy group; R$_2$ is monohydroxyalkyl having from 2 to 4 carbon atoms and wherein the corresponding leuco bases of the aromatic bases (I), the tautomers thereof, and the non-toxic pharmaceutically acceptable acid-addition salts thereof.

Another preferred embodiment of the present invention may be represented by the following general formula:

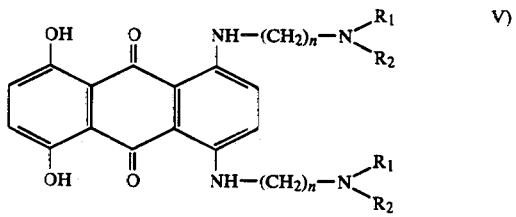

wherein n is an integer from 2 to 4, inclusive, and $R_1$ and $R_2$ are as defined for the preceding preferred embodiment with the proviso that the ratio of the total number of carbon atoms to the sum of total number of oxygen atoms plus the total number of nitrogen atoms in each of the side chains at the 1-position and the 4-position may not exceed four. This preferred embodiment also includes the corresponding leuco bases of the aromatic bases (V), the tautomers thereof, and the non-toxic pharmaceutically acceptable acid-addition salts thereof.

Also embraced within the purview of the present invention are therapeutic compositions of matter useful for ameliorating cancer diseases in mammals and containing certain 5,8-dihydroxy-1,4-bis(substituted-amino)anthraquinones (or the leuco bases and non-toxic acid-addition salts thereof) which may be represented by the following structural formula:

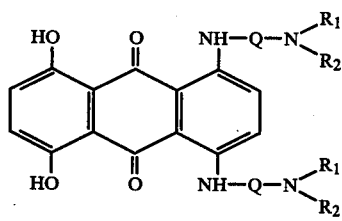

wherein $R_1$ is hydrogen or alkyl having from 1 to 4 carbon atoms, $R_2$ is hydrogen or alkyl having from 1 to 4 carbon atoms, $R_1$ and $R_2$ taken together with their associated N(itrogen) is as hereinbefore defined for $R_3$ and $R_4$ taken together with their associated N(itrogen), and Q is as hereinbefore defined. This aspect of the invention includes the novel compositions of matter and the method of inducing the regression and/or palliation of leukemia and related cancers in mammals therewith.

The active ingredients of the therapeutic compositions and the novel compounds of the present invention inhibit transplanted mouse tumor growth and induce regression and/or palliation of leukemia and related cancers in mammals when administered in amounts ranging from about 5 mg to about 200 mg. per kilogram of body weight per day. A preferred dosage regimen for optimum results would be from about 5 mg. to about 50 mg. per kilogram of body weight per day, and such dosage units are employed that a total of from about 350 mg. to about 3.5 grams of the active compound for a subject of about 70 kg. of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular, or subcutaneous routes.

The active compounds may be orally administerd, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 milligrams of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol liquid polyethylene glycols, and mixtures thereof and in oils. Under ordinary conditions of storange and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lccithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg., with from about one to about 30 mg. being preferred. Expressed in proportions, the active compound is generally present in from about 0.1 to about 400 mg./ml. of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

Leuco-1,4-bis[(2-dimethylaminoethyl)amino]-5,8-dihydroxy-anthraquinone

A reaction mixture comprising 10.58 g. of N,N-dimethylethylenediamine, 60 ml. of N,N,N',N'-tetramethylethylenediamine and 10.96 g. of leuco-1,4,5,8-tetrahydroxyanthraquinone is flushed with nitrogen and stirred under nitrogen for 2 hours while heating with an oil bath kept at 49°–51° C. The mixture is allowed to cool under nitrogen. The solid is collected and washed with ethanol giving 14.78 g. of the desired product as a dark red-brown solid.

EXAMPLE 2

1,4-Bis[(2-dimethylaminoethyl)amino]-5,8-dihydroxyanthraquinone

A 12.00-g. portion of leuco-1,4-bis[(2-dimethylaminoethyl)amino]-5,8-dihydroxy-anthraquinone in 100 ml. of nitrobenzene is heated under reflux for 15 minutes and then filtered while hot. The filtrate is reheated to boiling, allowed to cool, and the solid is collected and washed with ethanol giving 8.44 g. of the desired product as blue-black crystals, mp. 236°–238° C.

EXAMPLE 3

Leuco-1,4-bis(2-morpholinoethylamino)-5,8-dihydroxyanthraquinone

A solution of 15.62 g. of N-(2-aminoethyl)morpholine in 40 ml. of N,N,N',N'-tetramethylethylenediamine is de-aerated by bubbling nitrogen through it for 15 minutes. A 10.97-g. portion of leuco-1,4,5,8-tetrahydroxyanthraquinone is added slowly with stirring and the suspension is treated as described in Example 1, giving 18.07 g. of the desired product as an olive solid, mpm 223°–227° C.

EXAMPLE 4

1,4-Bis(2-morpholinoethylamino)-5,8-dihydroxyanthraquinone

A 13.90-g. portion of leuco-1,4-bis(2-morpholinoethylamino)-5,8-dihydroxy-anthraquinone in 100 ml. of nitrobenzene is oxidized as described in Example 2 giving 10.30 g. of the desired product as black rods, mp. 241°–243° C.

EXAMPLE 5

Leuco-1,4-bis[(2-diethylaminoethyl)amino]-5,8-dihydroxyanthraquinone

The procedure of Example 3 is repeated using 13.95 g. of N,N-diethylethylenediamine in place of the N-(2-aminoethyl)morpholine, giving 13.97 g. of the desired product as a red-brown solid, mp. 182°–185° C.

EXAMPLE 6

1,4-Bis[(2-diethylaminoethyl)amino]-5,8-dihydroxyanthraquinone

A 10.90-g. portion of leuco-1,4-bis[(2-diethylaminoethyl)amino]-5,8-dihydroxyanthraquinone is oxidized as described in Example 2 giving 6.35 g. of the desired product as blue-black needles, mp. 202°–204° C.

EXAMPLE 7

Leuco-1,4-bis[2-(1-pyrrolidinyl)ethylamino]-5,8-dihydroxyanthraquinone

The procedure of Example 3 is repeated using 12.05 g. of N-2-pyrrolidinoethylamine, in place of the N-(2-aminoethyl)morpholine, and 80 ml. of N,N,N′,N′-tetramethylethylenediamine, giving 13.24 g. of the desired product as a red-brown solid, mp. 180°–185° C.

EXAMPLE 8

1,4-Bis[2-(1-pyrrolidinyl)ethylamino]-5,8-dihydroxyanthraquinone

An 8.61-g. portion of leuco-1,4-bis[[2-(1-pyrrolidinyl)ethyl]amino]-5,8-dihydroxyanthraquinone is oxidized as described in Example 2. The reaction mixture is evaporated to dryness and the residue recrystallized from toluene, giving 5.12 g. of the desired product as blue-black crystals, mp. 193°–196° C.

EXAMPLE 9

Leuco-1,4-bis[2-(methylamino)ethylamino]-5,8-dihydroxyanthraquinone

The procedure of Example 7 is repeated using 8.90 g. of N-methylethylenediamine in place of the N-2-pyrrolidinoethylamine, giving 13.73-g. of the desired product as a dark green solid, mp. 157°–160° C.

EXAMPLE 10

Leuco-1,4-bis[(3-dimethylaminopropyl)amino]-5,8-dihydroxyanthraquinone

Nitrogen is bubbled through an 80-ml. portion of dimethylaminopropylamine for 15 minutes. A 10.97-g. portion of leuco-1,4,5,8-tetrahydroanthraquinone is added slowly with stirring. The mixture is heated under nitrogen at 50°–52° C. for 2 hours and then allowed to cool. The solid is collected and washed with cold ethanol giving 5.59-g. of dark, orange-red crystals, mp. 115°–118° C.

EXAMPLE 11

1,4-Bis[(3-dimethylaminopropyl)amino]-5,8-dihydroxyanthraquinone

A suspension of 6.00-g. of leuco-1,4-bis[(3-dimethylaminopropyl)amino]-5,8-dihydroxyanthraquinone in 60 ml. of N,N,N′,N′-tetramethylethylenediamine is heated on a steam bath under reflux while air is bubbled in for 12 hours. The solution is cooled, producing a solid which is collected and washed twice with heptane and once with petroleum ether. This solid is recrystallized by extracting with 350 ml. of hot heptane, filtering and concentrating to 300 ml. Crystallization and washing with petroleum ether gives 3.72 g. of the desired product as black needles, mp. 154°–157° C.

EXAMPLE 12

Leuco-1,4-bis(2-aminoethylamino)-5,8-dihydroxyanthraquinone

A reaction mixture comprising 10.97-g. of leuco-1,4,5,8-tetrahydroxyanthraquinone in 80 ml. of de-aerated N,N,N′,N′-tetramethylethylenediamine containing 7.22 g. of ethylenediamine is heated and stirred under nitrogen at 48°–50° C. for one hour. The mixture is allowed to stand under a slow flow of nitrogen, producing a solid which is collected and washed with ethyl acetate, acetonitrile and petroleum ether giving 13.8 g. of the desired product as a red-black solid.

EXAMPLE 13

Leuco-1,4-bis(3-aminopropylamino)-5,8-dihydroxyanthraquinone

A suspension of 10.97 g. of leuco-1,4,5,8-tetrahydroxyanthraquinone in a de-aerated solution of 8.90 g. of 1,3-diaminopropane in 80 ml. of N,N,N′,N′-tetramethylethylenediamine is stirred and heated at 49° C. for one hour under nitrogen, then allowed to cool. The resulting solid is collected and washed with cold ethanol giving 14.21 g. of the desired product as a black solid.

EXAMPLE 14

Leuco-1,4-bis[2-(2-hydroxyethylamino)ethylamino]-5,8-dihydroxyanthraquinone

A suspension of 12.5 g. of 2-(2-aminoethylamino)ethanol in 40 ml. of N,N,N′,N′-tetramethylethylenediamine is stirred and de-aerated by bubbling nitrogen in for 15 minutes. A 10.97-g. portion of leuco-1,4,5,8-tetrahydroxyanthraquinone is gradually added with stirring. The suspension is heated and stirred under nitrogen in an oil bath at 50°–52° C. for 5 hours. The mixture is allowed to stand and cool under nitrogen for 12 hours. The solid is collected by decantation, macerated in ethanol, collected and washed with ethanol giving 15.06 g. of the desired product as a green-gray solid, mp. 129°–131° C.

EXAMPLE 15

Leuco-1,4-bis[2-[di($\beta$-hydroxyethyl)amino]ethylamino]-5,8-dihydroxyanthraquinone A solution of 17.8 g. of N,N-di(2-hydroxyethyl)ethylenediamine in 100 ml. of methanol is cooled with an ice bath, stirred, and de-aerated by bubbling in nitrogen for 15 minutes. A 10.97-gram portion of leuco-1,4,5,8-tetrahydroxyanthraquinone is gradually added with stirring and continued cooling. The suspension is heated and stirred under nitrogen in an oil bath at 50°–52° C. for one hour and the mixture is then allowed to stand and cool under nitrogen overnight. The solid is collected and washed with ethanol giving 14.8 g. of a red-brown solid, m.p. 165°–168° C.

EXAMPLE 16

1,4-Bis[2-(methylamino)ethylamino]-5,8-dihydroxyanthraquinone dihydrochloride

To a suspension of 11.60 g. (0.03 mole) of leuco-1,4-bis[2-(methylamino)ethylamino]-5,8-dihydroxyanthraquinone in 200 ml. of 2-methoxyethanol was added gradually with stirring 15 ml. of 8N ethanolic hydrogen chloride. The system was chilled with an ice bath and stirred as 7.50 g. (0.0305 mole) of chloranil powder was gradually added. The mixture was stirred overnight at room temperature and diluted with 600 ml. of ether. The solid was collected and washed with tetrahydrofuran. The product (14.16 g.) was recrystallized by dissolving it in 130 ml. of water and adding 650 ml. of acetone to give 13.15 g. of a blue-black solid.

EXAMPLE 17

1,4-Bis[2-(2-aminoethylamino)ethylamino]-5,8-dihydroxyanthraquinone

Following the general procedure of Example 3, a mixture of 10.97-g. of leuco-1,4,5,8-tetrahydroxyanthraquinone, 80 ml. of N,N,N',N'-tetramethylethylenediamine and 21.84-g. (0.24 mole) of diethylenetriamine soon gave a thick, congealed mass which prevented effective stirring so the reaction time was extended to 24 hours. The mixture was allowed to cool and the supernatent liquid was decanted and discarded. A solution of the congealed mass in 100 ml. of methanol was filtered, then allowed to oxidize in the air for four days in a partially covered flask. The gelatinous mass which had separated became solid when the oxidation mixture was agitated with 200 ml. of acetonitrile and then allowed to stand for one hour. After the solid was collected and washed first with acetonitrile, then with ether, it amounted to 10.88 g. of a blue-black powder.

EXAMPLE 18

Leuco-1,4-bis(4-aminobutylamino)-5,8-dihydroxyanthraquinone

Following the general procedure of Example 3 but using 45 ml. of 1,4-diaminobutane as the primary amine component, there was obtained 12.20 g. of product as a dull grey-green solid.

EXAMPLE 19

Leuco-1,4-bis[2-dimethylaminopropylamino]-5,8-dihydroxyanthraquinone

The reaction of 12.26 g. of 2-dimethylaminopropylamine with 10.97 g. of leuco-1,4,5,8-tetrahydroxyanthraquinone in 100 ml. of ethanol for one hour by the procedure of Example 1 gives 7.29 g. of red-brown crystals.

EXAMPLE 20

Leuco-1,4-bis[2-(2-methylaminoethylamino)ethylamino]-5,8-dihydroxyanthraquinone

To a solution of 14.10 g. of 1-methyl diethylenetriamine in 50 ml. of ethanol and 40 ml. of N,N,N',N'-tetramethylethylenediamine is added 10.97 g. of leuco-1,4,5,8-tetrahydroxyanthraquinone as in Example 1. The mixture is heated at 50° and stirred under nitrogen for one hour, chilled with an ice bath, the solid collected and washed with cold ethanol to give 7.23 g. of green-black crystals, m.p. 108°–111° C.

EXAMPLE 21

Leuco-1,4-bis[2-(2-dimethylaminoethylamino)ethylamino]-5,8-dihydroxyanthraquinone The reaction of N-(dimethylaminoethyl)ethylenediamine with leuco-1,4,5,8-tetrahydroxyanthraquinone by the procedure of Example 20 gives the title compound.

EXAMPLE 22

Leuco-1,4-bis[2-(1-piperazinyl)ethylamino]-5,8-dihydroxyanthraquinone

The procedure of Example 20 applied to 15.50 g. of N-(2-aminoethyl)piperazine gives 3.92 g. of a black powder which does not melt by 350° C. and is discarded. The mother liquor and ethanol washes, on standing and partly evaporating during two weeks in an unstoppered flask, deposit a solid which is collected and washed with ethanol to give 6.19 g. of the title compound as a black solid, m.p. 200°–203° C.

EXAMPLE 23

1,4-Bis(2-aminoethylamino)-5,8-dihydroxyanthraquinone dihydrochloride

Oxidation with chloranil of 28.25 g. of the product of Example 12 by the procedure of Example 16 gives 29.66 g. of a crude, blue-black solid which is then extracted by stirring for 14 hours with 800 ml. of water. Solids are removed by centrifugation and the supernatent solution freeze-dried, leaving 16.38 g. of a blue-black solid which is unmelted by 350° C.

EXAMPLE 24

1,4-Bis[2-(2-hydroxyethylamino)ethylamino]-5,8-dihydroxyanthraquinone Dihydrochloride Chloranil oxidation of 17.86 g. of the product of Example 14 by the procedure of Example 16 gives (without recrystallization) 21.34 g. of blue-black solid, m.p. 203°–205° C.

EXAMPLE 25

1,4-Bis[2-(2-methylaminoethylamino)ethylamino]-5,8-dihydroxyanthraquinone Tetrahydrochloride The product of Example 20 (11.70 g.) is oxidized with chloranil by the procedure of Example 16, giving 18.03 g. of blue-black solid, m.p. 190°–203° C.

EXAMPLE 26

1,4-Bis[2-(2-hydroxyethylamino)ethylamino]-5,8-dihydroxyanthraquinone

In a modification of the synthesis of Example 14 the solvent used is 100 ml. of ethanol. The mother liquor from the leuco product is allowed to stand for two weeks in an unstoppered flask, whereupon the oxidized product separates. It is collected and washed with ethanol, then recrystallized from ethanol, giving blue-black crystals, m.p. 175°–177° C.

EXAMPLE 27

Leuco-1,4-bis[3-(2-hydroxyethylamino)-1-propylamino]-5,8-dihydroxyanthraquinone

The procedure of Example 15 is used with a solution of 14.18 g. of 2-(3-aminopropylamino)ethanol in 100 ml. of ethanol. The resulting solution is filtered and the filtrate diluted with 300 ml. of ether, precipitating the product as a goo. After decantation of the supernatent solution the goo is caused to crystallize by agitating it with 100 ml. of tetrahydrofuran. Washing with ethanol gives 12.56 g. of green-black solid, m.p. 101°–104° C.

EXAMPLE 28

1,4-Bis[3-(2-hydroxyethylamino)-1-propylamine]-5,8-dihydroxyanthraquinone dihydrochloride Oxidation of 9.95 g. of leuco-1,4-bis[3-(2-hydroxyethylamino)propylamino]-5,8-dihydroxyanthraquinone with chloranil as in Example 16 gives 11.70 g. of a blue solid which does not melt by 350° C.

EXAMPLE 29

Leuco-1,4-bis[2-(3-hydroxy-1-propylamino)ethylamino]-5,8-dihydroxyanthraquinone

The procedure of Example 15 is paralleled with 14.18 g. of N-(3-hydroxypropyl)ethylenediamine in 100 ml. of ethanol to give 14.63 g. of red-brown crystals, m.p. 58°–60° C.

EXAMPLE 30

1,4-Bis[2-(3-hydroxy-1-propylamino)ethylamino]-5,8-dihydroxyanthraquinone dihydrochloride Chloranil oxidation of 10.77 g. of the product of Example 29 by the procedure of Example 16 yielded 11.64 g. of a dark blue solid, m.p. 210°–216° C.

EXAMPLE 31

Leuco-1,4-bis[2-(2-hydroxy-1-propylamino)ethylamino]-5,8-dihydroxyanthraquinone

With 14.18 g. of 1-(2-aminoethylamino)-2-propanol in 100 ml. of ethanol the procedure of Example 15 yields 17.61 g. of green-black crystals, m.p. 50°–60° C.

EXAMPLE 32

1,4-Bis[2-(2-hydroxy-1-propylamino)ethylamino]-5,8-dihydroxyanthraquinone dihydrochloride A filtered solution of 14.44 g. of leuco-1,4-bis[2-(2-hydroxy-1-propylamino)ethylamino]-1,4-dihydroxyanthraquinone in 215 ml. of 2-methoxyethanol is oxidized with 7.65 g. of chloranil by the procedure of Example 16, affording 16.75 g. of purple solid, m.p. 177°–185° C.

EXAMPLE 33

Leuco-1,4-bis[2-[2-(2-hydroxyethylamino)ethylamino]ethylamino]-5,8-dihydroxyanthraquinone The procedure of example 15 used with a solution of 17.67 g. of 2-[2-(2-aminoethylamino)ethylamino]ethanol in 100 ml. of methanol gives a solution which is filtered, then diluted with 300 ml. of ether, precipitating a goo which hardens on standing overnight. Hardening is completed by thorough maceration of the solid in the solvent. The solid is collected and washed with ether, yielding 16.82 g. of a green-black solid. This solid remains granular if stored at −25° C., but coalesces into a solid cake if stored at 25° C.

EXAMPLE 34

1,4-Bis[2-[2-(2-hydroxyethylamino)ethylamino]ethylamino]-5,8-dihydroxyanthraquinone tetrahydrochloride Chloranil oxidation of 12.10 g. of the product of Example 33 by the method of Example 16, including three additional washings of the solid with methanol, gives 12.46 g. of dark blue, solid product.

EXAMPLE 35

1,4-Bis[2-(2,3-dihydroxypropylamino)ethylamino]-5,8-dihydroxyanthraquinone dihydrochloride By the procedure of Example 15 a solution of 16.10 g. of 3-(2-aminoethylamino)-1,2-propanediol [A. R. Surrey, C. M. Suter and J. S. Buck, J. Am. Chem. Soc., 74, 4102(1952)] in 100 ml. of methanol gives a goo which is separated from solvent by chilling with an ice bath, then decanting. The goo is washed four times by stirring 1.5 hours at 25° with 100-ml. portions of methanol, chilling with an ice bath, then decanting. A filtered solution of the goo in 280 ml. of 2-methoxyethanol is oxidized with 10.01 g. of chloranil by the method of Example 16. The product is additionally washed with ethanol, giving 15.25 g. of a blue-black solid, m.p. 191°–193° C.

EXAMPLE 36

Leuco-1,4-bis[2-(1-aziridino)ethylamino]-5,8-dihydroxyanthraquinone

With 10.33 g. of N-(2-aminoethyl)aziridine in 80 ml. of N,N,N',N'-tetramethylethylenediamine the procedure of Example 15 gives a stiff gum. The next day the supernatent solution is discarded, 100 ml. of ether is added and the gum periodically macerated therein for another day, when the gum is mostly hardened. Hardening is completed by maceration during three washings of the solid with ether, giving 17.66 g. of blue-black, granular powder.

EXAMPLE 37

1,4-Bis[2-(1-aziridino)ethylamino]-5,8-dihydroxyanthraquinone

To a suspension of 4.10 g. of the product of Example 36 in 40 ml. of chlorodorm is added a solution of 1.74 g. of diethyl azodicarboxylate in 25 ml. of chloroform. The mixture is stirred for 20 minutes, the resulting dark blue solution is filtered, and the filtrate is evaporated at ≦30°. A solution of the residue in 40 ml. of chloroform is stirred five minutes with 2 g. of decolorizing carbon, filtered and washed through with another 25 ml. of chloroform. Addition of 100 ml. of ether to the filtrates precipitates a gum which is eliminated by decantation-filtration. The filtrates deposit crystals which are washed sparingly with acetone. The chloroform-ether mother liquor, chilled at −60° C., deposits a second crop of crystals which is washed with ether and with methanol. A solution of both crops of crystals in 20 ml. of chloroform is stirred with decolorizing carbon, filtered, evaporated at ≦25° C., to a volume of 5 ml., diluted with 20 ml. of ether, then chilled at −60° C. The resulting blue-black crystals, washed with ether, amount to 0.64 g., m.p. 168°–170° C. In thin-layer chromatography on silica gel the product is moved as a blue spot by chloroform-triethylamine-methanol, 27/3/1 (ratios by volume).

EXAMPLE 38

1,4-Bis[2-[2-(1-morpholino)ethylamino]ethylamino]-5,8-dihydroxyanthraquinone tetrahydrochloride A solution of 20.80 g. of N-(morpholinoethyl)ethylenediamine in 100 ml. of ethanol is used in the procedure of Example 15 to give a solution which is filtered and diluted with 900 ml. of ether, precipitating a goo. The supernatent solution is decanted, the goo dissolved in 175 ml. of 2-methoxyethanol and oxidized with 5.29 g. of chloranil by the method of Example 16, giving 17.7 g. of dark blue solid.

EXAMPLE 39

Leuco-1,4-Bis[2-(acetamido)ethylamino]-5,8-dihydroxyanthraquinone

A solution of 12.26 g. of N-acetylethylene diamine in 100 ml. of ethanol in the procedure of Example 15 gives 15.27 g. of dark, red-brown solid, m.p. 125° C.

EXAMPLE 40

1,4-Bis[2-(acetamido)ethylamino]-5,8-dihydroxyanthraquinone

A suspension of 11.95 g. of leuco-1,4-bis[2-(acetamido)ethylamino]-5,8-dihydroxyanthraquinone is oxidized with 6.76 g. of chloranil during 61 hours by the method of Example 16, giving a very acidic hydrochloride salt which is vonverted to the free base by four washings with water. Crystallization from 110 ml. of dimethyl sulfoxide (boiling only 2 minutes and not attempting a hot filtration), then washing with dimethyl sulfoxide and with ethanol gives 7.76 g. of blue-black solid, m.p. 273°–274° C.

EXAMPLE 41

1,4-Bis[2-[N-(2-hydroxyethyl)triflouroacetamido]ethylamino]-5,8-dihydroxyanthraquinone A suspension of 1.50 g. of 1,4-bis[2-(2-hydroxyethylamino)ethylamino]-5,8-dihydroxyanthraquinone in 75 ml. of ethyl triflouroacetate and 75 ml. of methanol is stirred for 10 minutes. Evaporation of the resulting solution in vacuo at 30° C. leaves a residue which is washed and macerated with methylene chloride, giving 2.11 g. of blue-black solid, m.p. 162° C.

EXAMPLE 42

1,4-Bis[2-amino-2-carboxyethylamino]-5,8-dihydroxyanthraquinone.3/4 HCl

To a solution of 6.23 g. of dl-$\alpha,\beta$-diaminopropionic acid in 30 ml. of warm water is added 1.078 g. of lithium hydroxide and 60 ml. of dimethyl sulfoxide. The system is flushed with nitrogen and 4.12 g. of leuco-1,4,5,8-tetrahydroxyanthraquinone is added gradually with stirring. The mixture is stirred and heated with an oil bath at 50°, first for 15 hours under nitrogen, then for 21 hours as the initial product is oxidized by bubbling in a stream of air. Thin-layer chromatography on silica gel with methanol-water-concentrated ammonia (25/5/1 by volume) shows all the product spots to be blue when the oxidation is complete. After the mixture is cool the solids are removed by filtration and washed once with dimethyl sulfoxide-water (2/1). Addition of 400 ml. of methanol to the filtrates precipitates a solid which is collected and washed with methanol. Further washing with a total of 13 ml. of 0.01N aqueous acetic acid dissolves virtually all of the solid. Addition of 3 ml. of concentrated hydrochloric acid to the acetic acid filtrates precipitates a blue-black solid which is washed with acetone to give 0.24 g. of the product.

EXAMPLE 43

Leuco-1,4-bis[2-(2-methoxyethylamino)ethylamino]-5,8-dihydroxyanthraquinone

An ethanol solution of N-(2-methoxyethyl)ethylendiamine (U.S. Pat. No. 3,454,640) reacts in the procedure of Example 15 to give the title compound.

EXAMPLE 44

1,4-Bis[2-(1,3-oxazolidin-1-yl)ethylamino]-5,8-dihydroxyanthraquinone

A solution of 1.62 g. of 37% aqueous formaldehyde solution in 50 ml. of water is stirred overnight with 4.44 g. of 1,4-bis[2-(2-hydroxyethylamino)ethylamino]-5,8-dihydroxyanthraquinone. The resulting solid is washed with water to give the product.

EXAMPLE 45

1,4-Bis[2-(tetrahydro-1,3-oxazin-1-yl)ethylamino]-5,8-dihydroxyanthraquinone

A solution of 1.62 ml. of 37% aqueous formaldehyde in 50 ml. of 0.4N aqueous sodium hydroxide is stirred overnight with 5.45 g. of 1,4-bis[2-(3-hydroxy-1-propylamino)ethylamino]-5,8-dihydroxyanthraquinone dihydrochloride. The product is obtained by washing the resulting solid with water.

EXAMPLE 46

1,4-Bis[2-(1,3-oxazolidin-2-one-1-yl)ethylamino]-5,8-dihydroxyanthraquinone

A solution of 0.020 g. of sodium in 25 ml. of methanol is stirred and heated under reflux overnight with 75 ml. of diethyl carbonate and 4.44 g. of 1,4-bis[2-(2-hydroxyethylamino)ethylamino]-5,8-dihydroxyanthraquinone. The mixture is allowed to cool. It is stirred with 0.1 ml. of acetic acid, the solid is collected by filtration and washed with methanol to give the product.

EXAMPLE 47

1,4-Bis[2-(1,3-oxazin-2-one-1-yl)ethylamino]-5,8-dihydroxyanthraquinone

A solution of 0.48 g. of sodium in 25 ml. of methanol is stirred and heated overnight with 75 ml. of diethyl carbonate and 5.45 g. of 1,4-bis[2-(3-hydroxy-1-propylamino)ethylamino]-5,8-dihydroxyanthraquinone dihydrochloride. After the mixture cools it is stirred with 0.1 ml. of acetic acid. The solid product is collected by filtration and washed with methanol and then with water.

EXAMPLE 48

1,4-Bis[2-[di($\beta$-hydroxyethyl)amino]ethylamino]-5,8-dihydroxyanthraquinone dihydrochloride Chloranil oxidation of 10.77 g. of the product of Example 15 by the method of Example 16 gives 11.64 g. of a dark blue solid, m.p. 216° C.

EXAMPLE 49

| Preparation of 50 mg. Tablets | | |
|---|---|---|
| Per Tablet | | Per 10,000 Tablets |
| 0.050 gm | 1,4-bis(3-aminopropylamino)-5,8-dihydroxyanthraquinone | 500 gm. |
| 0.080 gm. | Lactose | 800 gm. |

| Preparation of 50 mg. Tablets | | |
|---|---|---|
| Per Tablet | | Per 10,000 Tablets |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 1,4-bis(3-aminopropylamino)-5,8-dihydroxyanthraquinone, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 50

| Preparation of Oral Suspension | |
|---|---|
| Ingredient | Amount |
| Leuco-1,4-bis(3-aminopropylamino)-5,8-dihydroxyanthraquinone | 500 mg. |
| Sorbitol solution (70% N.F.) | 40 ml. |
| Sodium benzoate | 150 mg. |
| Saccharin | 10 mg. |
| Red dye | 50 mg. |
| Cherry flavor | 50 ml. |
| Distilled water qs ad | 100 ml. |

The sorbitol solution is added to 40 ml. of distilled water and the leuco-1,4-bis(3-aminopropylamino)-5,8-dihydroxyanthraquinone is suspended therein. The saccharin, sodium benzoate, flavor and dye are added and dissolved. The volume is adjusted to 100 ml. with distilled water. Each ml. of syrup contains 5 mg. of leuco-1,4-bis(3-aminopropylamino)-5,8-dihydroxyanthraquinone.

EXAMPLE 51

Preparation of Parenteral Solution

In a solution of 700 ml. of propylene glycol and 200 ml. of water for injection is suspended 20.0 grams of 1,4-bis[3-(dimethylamino)propylamino]-5,8-dihydroxyanthraquinone dihydrochloride with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 52

1,4-Bis[2-(2-hydroxyethylamino)ethylamino]-5,8-dihydroxyanthraquinone disuccinate salt A mixture of 222 mg. of 1,4-bis[2-(2-hydroxyethylamino)ethylamino]-5,8-dihydroxyanthraquinone, 118 mg. of succinic acid, and 50 ml. of ethanol is heated under reflux for 30 minutes to give the title compound.

EXAMPLE 53

1,4-Bis[2-(3-hydroxypropylamino)ethylamino]-5,8-dihydroxyanthraquinone dimalate salt A mixture of 228 mg. of 1,4-bis[2-(3-hydroxypropylamino)ethylamino]-5,8-dihydroxyanthraquinone, 134 mg. of DL-malic acid, and 50 ml. of ethanol is heated under reflux for 30 minutes to give the title compound.

EXAMPLE 54

1,4-Bis[2-(2-hydroxypropylamino)ethylamino]-5,8-dihydroxyanthraquinone dilactate salt A mixture of 228 mg. of 1,4-bis[2-(2-hydroxypropylamino)ethylamino]-5,8-dihydroxyanthraquinone, 120 mg. of 80% DL-lactic acid, and 10 ml. of ethanol is heated on a steam bath for 10 minutes, cooled treated with 50 ml. of acetone and cooled to obtain the title compound.

EXAMPLE 55

| Preparation of 50 mg. Tablets | | |
|---|---|---|
| Per Tablet | | Per 10,000 Tablets |
| 0.050 gm. | 1,4-Bis[2-(2-hydroxyethylamino)ethylamino]-5,8-dihydroxyanthraquinone dihydrochloride | 500 gm. |
| 0.080 gm | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 1,4-bis[2-(2-hydroxyethylamino)ethylamino]-5,8-dihydroxyanthraquinone dihydrochloride, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 56

| Preparation of Oral Suspension | |
|---|---|
| Ingredient | Amount |
| 1,4-Bis[2-(2-hydroxyethylamino)ethylamino]-5,8-dihydroxyanthraquinone dihydrochloride | 500 mg. |
| Sorbitol solution (70% N.F.) | 40 ml. |
| Sodium benzoate | 150 mg. |
| Saccharin | 10 mg. |
| Red dye | 50 mg. |
| Cherry flavor | 50 ml. |
| Distilled water qs ad | 100 ml. |

The sorbitol solution is added to 40 ml. of distilled water and the 1,4-bis[2-(2-hydroxyethylamino)ethylamino]-5,8-dihydroxyanthraquinone dihydrochloride is suspended therein. The saccharin, sodium benzoate, flavor and dye are added and dissolved. The volume is adjusted to 100 ml. with distilled water. Each ml.

of syrup contains 5 mg. of 1,4-bis[2-(2-hydroxyethylamino)ethylamino]-5,8-dihydroxyanthraquinone dihydrochloride.

EXAMPLE 57

1,4-Bis[2-(3-hydroxypropylamino)ethylamino]-5,8-dihydroxyanthraquinone diacetate salt A mixture of 228 mg. of 1,4-bis[2-(3-hydroxypropylamino)ethylamino[-5,8-dihydroxyanthraquinone, 60 mg. of glacial acetic acid, and 50 ml. of ethanol is heated under reflux for 30 minutes to give the title compound.

EXAMPLE 58

1,4-Bis[2-(2-hydroxypropylamino)ethylamino]-5,8-dihydroxyanthraquinone diacetate salt A mixture of 228 mg. of 1,4-bis[2-(2-hydroxypropylamino)ethylamino]-5,8-dihydroxyanthraquinone, 60 mg. of glacial acetic acid, and 10 ml. of ethanol is heated on a steam bath for 10 minutes, cooled, treated with 50 ml. of acetone and cooled to obtain the title compound.

We claim:

1. A compound selected from the group consisting of 1,4-bis[2-(2-aminoethylamino)ethylamino]-5,8-dihydroxyanthaquinone, the leuco base and tautomer thereof and the pharmacologically acceptable acid-addition salts thereof.

2. A compound selected from the group consisting of 1,4-bis[2-(2-methylaminoethylamino)ethylamino]-5,8-dihydroxyanthraquinone, the leuco base and tautomer thereof and the pharmacologically acceptable acid-addition salts thereof.

3. A compound selected from the group consisting of 1,4-bis[2-(2-dimethylaminoethylamino)ethylamino]-5,8-dihydroxyanthraquinone, the leuco base and tautomer thereof and the pharmacologically acceptable acid-addition salts thereof.

4. A compound selected from the group consisting of 1,4-bis[2-(2,3-dihydroxypropylamino)ethylamino]-5,8-dihydroxyanthraquinone, the leuco base and tautomer thereof and the pharmacologically acceptable acid-addition salts thereof.

5. A compound selected from the group consisting of 1,4-bis[2-(N-($\beta$-hydroxyethyl)trifluoroacetamido)ethylamino]-5,8-dihydroxyanthraquinone, the leuco base and tautomer thereof and the pharmacologically acceptable acid-addition salts thereof.

* * * * *